United States Patent [19]  [11]  4,265,883
Cameron  [45]  May 5, 1981

[54] COMPOSITION AND PROCESS FOR TREATING UTERINE PROLAPSE

[76] Inventor: Mable R. Cameron, 7207 S. Bennett Ave., Chicago, Ill. 60649

[21] Appl. No.: 80,640

[22] Filed: Oct. 1, 1979

[51] Int. Cl.³ .................. A61K 33/06; A61K 9/06; A61K 31/245
[52] U.S. Cl. .................. 424/154; 424/28; 424/310; 424/358
[58] Field of Search .................. 424/28, 154, 310, 358

[56] References Cited

U.S. PATENT DOCUMENTS

| Patent No. | Date | Inventor | Class |
|---|---|---|---|
| 120,879 | 11/1871 | Irwin | 424/154 |
| 139,315 | 5/1873 | Hucks | 424/154 |
| 149,455 | 4/1874 | Epperly | 424/154 |
| 177,387 | 5/1876 | Emerson et al. | 424/154 |
| 203,038 | 4/1878 | Hebdon | 424/154 |
| 208,883 | 10/1878 | Berlin | 424/154 |
| 243,800 | 7/1881 | Roth | 424/154 |
| 273,552 | 3/1883 | Larsen | 424/154 |
| 295,078 | 3/1884 | Thatcher | 424/154 |
| 327,267 | 9/1885 | Hecker et al. | 424/154 |
| 673,769 | 5/1901 | Ford | 424/154 |
| 1,372,496 | 3/1921 | Finigan | 424/154 |
| 1,504,911 | 8/1924 | Schindler-Jenny | 424/154 |
| 1,558,160 | 10/1925 | Gearhart | 424/154 |
| 2,372,807 | 4/1945 | Brown | 424/154 |
| 2,890,987 | 6/1959 | Hilfer | 424/154 |
| 3,180,827 | 4/1965 | Martinek et al. | 424/357 |
| 3,856,941 | 12/1974 | Turner | 424/154 |
| 4,005,191 | 1/1977 | Clark | 424/154 |

*Primary Examiner*—Shep K. Rose
*Attorney, Agent, or Firm*—Bernard L. Kleinke

[57] ABSTRACT

A process of treating a female having uterine prolapse which comprises topically applying to the uterus an ointment comprising alum, glycerine and a soft solid such as a hydrogenated vegetable oil, petroleum jelly or lard, preferably also comprising epsom salt and a local anesthetic such as tetracaine hydrochloride. The composition is also useful for treating sores, boils and hemorrhoids, and may be applied directly or as a gauze sheet having the composition on it.

10 Claims, No Drawings

COMPOSITION AND PROCESS FOR TREATING UTERINE PROLAPSE

The invention related to a composition and process for treatment of a prolapse of a uterus, and more particularly relates to an ointment for contracting or shrinking a prolapsed uterus.

Hitherto, so far as is known to applicant, prolapse of a uterus can only be relieved surgically. Applicant has invented a composition which when topically applied to a uterus under prolapse will shrink the fallen and expanded uterus without surgical treatment.

In accordance with this invention the composition comprises an ointment essentially comprising alum, glycerol and a soft solid carrier. It also preferably contains epsom salt (magnesium sulfate) and a local anesthetic such as, for example, procaine hydrochloride.

The alum is preferably ammonium alum (aluminum ammonium sulfate) although aluminum potassium sulfate may also be used.

The soft solid may, for example, be a fat such as lard, hydrogenated vegetable oil or petroleum jelly. This acts as a carrier and diluent and is used in amount sufficient to form an ointment when used with the other ingredients.

The glycerol (glycerine) acts as a solvent for the alum and the epsom salts. Alum and epsom salts in powder form are dissolved in the glycerine.

The epsom salts may be omitted, but have been found to have a healing and soothing effect.

The local anesthetic likewise may be omitted but its pain-killing effect is generally desired by the patient.

The composition is preferably coated on a gauze pad and applied by placing it on the sore area of the uterus. The gauze pad may have a string attached to it for convenient removal. Also, there may be used a cardboard tube for inserting. These may be sold together as a kit.

Suitable and preferred proportions of ingredients and concentration of alum with solvent and carrier in percent by weight are given below:

|  | Suitable | Preferred |
|---|---|---|
| Alum | 10–30 | 15–22 |
| Glycerine | 10–40 | 15–35 |
| Soft solid | 50–70 | 50–70 |
| Magnesium sulfate | 0–25 | 10–25 |
| Tetracaine hydrochloride | 0–2 | 1–2 |

Following are examples of compositions and dosage amounts suitable for the treatment of prolapse of the uterus of women.

The time of treatment for the examples given was 12 hours, but a longer period of time, such as three days, may be used without harmful effect. Also for mild cases, 6 hours or less is effective.

EXAMPLE 1

Small dose (¾ teaspoonful—equal to 2.5 grams)

| Ammonium alum | 3.8 grams |
|---|---|
| Glycerine | 3.8 grams |
| Crisco (hydrogenated vegetable oil) | 11.0 grams |
| Magnesium sulfate | 2.5 grams |
| Tetracaine hydrochloride (THC) | .8 gram |

EXAMPLE 2

Intermediate dose (1 teaspoonful)

| Ammonium alum | 4.5 grams |
|---|---|
| Glycerine | 3.0 grams |
| Crisco shortening | 26.9 grams |
| Magnesium sulfate | 2.8 grams |
| THC | 1.1 grams |

EXAMPLE 3

Large dose (1 tablespoonful)

| Ammonium alum | 10.5 grams |
|---|---|
| Glycerine | 9.0 grams |
| Crisco shortening | 41.0 grams |
| Magnesium sulfate | 9.2 grams |
| THC | 1.4 grams |

EXAMPLE 4

Dose for females 5–16 years old

| Ammonium alum | 70.4 grams |
|---|---|
| Glycerine | 124.0 grams |
| Crisco shortening | 200.0 grams |
| Magnesium sulfate | 52.8 grams |

Applicant discovered that the composition of this invention when topically applied to the prolapsed uterus of a female mammal would contract or shrink the uterus in an effective and safe manner when used in the amounts and proportions disclosed in this application for this purpose. The composition is also useful in alleviating pain on sore areas on the body of any mammal and is helpful in treating hemorrhoids and boils.

A suitable dose for treating hemorrhoids is as follows:

| Alum | 6.5 grams |
|---|---|
| Glycerine | 11.3 grams |
| Crisco shortening | 22.0 grams |
| Epsom salt | 5.0 grams |
| THC | 1.0 gram |

I claim:

1. The process of treating a female having uterine prolapse which comprises topically applying to the uterus an effective contracting amount of a composition consisting essentially of an alum selected from the group of aluminum ammonium sulfate and aluminum potassium sulfate, glycerine in amount sufficient to dissolve the alum, and a pharmaceutically acceptable soft solid carrier in amount sufficient to produce an ointment.

2. The process of claim 1 in which the soft solid is a hydrogenated vegetable oil.

3. The process of claim 1 in which the alum is aluminum ammonium sulfate.

4. The process of claim 1 in which magnesium sulfate is also present.

5. The process of claim 1 in which the alum is present in 10–30% by weight, the glycerine in 10–40%, and the soft solid is 50–70%.

6. A composition suitable for treating prolapse of a uterus to contract same which consists essentially of an ointment comprising an effective contracting amount of an alum selected from the group consisting of aluminum ammonium sulfate and aluminum potassium sulfate, glycerine in amount sufficient to dissolve the alum, and a pharmaceutically acceptable soft solid carrier in amount sufficient to produce an ointment.

7. An ointment according to claim 6 comprising 10–30% alum, 10–40% glycerine, and 50–70% of a soft solid.

8. An ointment according to claim 7 in which the soft solid is a hydrogenated vegetable oil.

9. A composition in accordance with claim 6 having approximately the following composition in percent by weight:

| | |
|---|---|
| Ammonium alum | 15–22 |
| Glycerine | 15–35 |
| Hydrogenated vegetable oil | 50–70 |
| Magnesium sulfate | 10–25 |

10. The composition in accordance with claim 9 in which tetracaine hydrochloride is also present in amount to act as a local anesthetic.

* * * * *